(12) United States Patent
Raderman (10) Patent No.: US 9,867,859 B2
(45) Date of Patent: *Jan. 16, 2018

(54) METHOD FOR INCREASING CANNABINOL CONTENT IN A LIPID-BASED EXTRACT OF CANNABIS

(71) Applicant: Raderman Holdings, LLC, Jamestown, CO (US)

(72) Inventor: Joshua Michael Raderman, Boulder, CO (US)

(73) Assignee: Raderman Holdings, LLC, Jamestown, CO (US)

( * ) Notice: Subject to any disclaimer, the term of this patent is extended or adjusted under 35 U.S.C. 154(b) by 242 days.

This patent is subject to a terminal disclaimer.

(21) Appl. No.: 15/043,604

(22) Filed: Feb. 14, 2016

(65) Prior Publication Data

US 2017/0020943 A1    Jan. 26, 2017

Related U.S. Application Data

(63) Continuation of application No. 14/588,150, filed on Dec. 31, 2014, now Pat. No. 9,259,449.

(60) Provisional application No. 61/964,538, filed on Jan. 7, 2014.

(51) Int. Cl.
  *A61K 36/00*   (2006.01)
  *A61K 36/185*  (2006.01)
  *A61K 31/05*   (2006.01)
  *A61K 47/44*   (2017.01)
  *A61K 9/00*    (2006.01)
  *A61K 9/48*    (2006.01)

(52) U.S. Cl.
  CPC .......... *A61K 36/185* (2013.01); *A61K 9/0014* (2013.01); *A61K 9/0053* (2013.01); *A61K 9/48* (2013.01); *A61K 31/05* (2013.01); *A61K 47/44* (2013.01); *A61K 2236/00* (2013.01); *A61K 2236/37* (2013.01); *A61K 2236/39* (2013.01); *A61K 2236/53* (2013.01); *A61K 2236/55* (2013.01)

(58) Field of Classification Search
  CPC ....................................................... A61K 36/00
  USPC ....................................................... 424/725
  See application file for complete search history.

(56) References Cited

U.S. PATENT DOCUMENTS

2006/0160888 A1   7/2006   Kottayil et al.
2014/0357708 A1   12/2014  Murty et al.

FOREIGN PATENT DOCUMENTS

WO   2012033478 A1   3/2012
WO   2012071389 A2   5/2012

*Primary Examiner* — Michael V Meller
(74) *Attorney, Agent, or Firm* — Kevin H. Fortin (57) ABSTRACT

A method for modifying cannabinol (CBN) to trans-Δ9-tetrahydrocannabinol (THC) content in a lipid-based extract of *cannabis* to yield a low-THC product. The method includes providing a lipid-based extract of *cannabis* containing THC, heating the lipid-based extract at 1 atm of pressure to 157 to 160° C. to vaporize a first portion of the THC, and converting a second portion of the THC to CBN by heating the lipid-based extract to between 130° C.-150° C. for at least 10 min. In one embodiment the step of vaporizing occurs after the step of converting to remove the trans-Δ9-tetrahydrocannabinol from the product.

9 Claims, 5 Drawing Sheets

METHOD FOR INCREASING CANNABINOL CONTENT IN A LIPID-BASED EXTRACT OF CANNABIS

PRIORITY CLAIM

This patent application is a continuation application of co-pending U.S. patent application Ser. No. 14/588,150, which claims the benefit of U.S. Provisional Patent Application Ser. No. 61/964,538, filed 7 Jan. 2014, the disclosures of these patent applications are incorporated herein by reference.

FIELD OF THE INVENTION

This invention relates to ways of extracting and concentrating cannabinoids from plant substrates including hemp, and particularly ways of modifying ratios of various cannabinoids including trans-Δ9-tetrahydrocannabinol (THC), Cannabinol (CBN) and Cannabidiol (CBD).

BACKGROUND OF THE INVENTION

U.S. Patent Publication No. US 2006/0160888 A1 to Kottayil et al. describes a Dronabinol formulation that is shelf stable and FDA approved. This is a pharmaceutical drug prescribed for anti-nausea in chemotherapy patients. The cannabinoid solution is in an oil-based carrier mixture having stabilizing amount of one or more anti-oxidants and other organic bases. The oil used is may include coconut oil in one embodiment. The formulation can be packaged in a soft gelatin capsule. The particular formulation yields a shelf life of up to two years. Dronabinol is available in natural and synthetic form. In natural form, THC-acid is extracted using chromatography and synthetically converted to Dronabinol.

Coconut oil is used as one of many possible oils in formulating the extracted cannabinoid.

One drawback of the Kottayil et al. invention is that isolated cannabinoids do not always achieve the therapeutic functionality as well as a whole plant extract containing a range of cannabinoids.

U.S. Patent Publication No. U.S. 2012/0046352 A1 to Hospodor describes a method for controlled decarboxylation of cannabinoids, namely Tetrahydrocanabinol acid (THC-A) to THC. Decarboxylation is facilitated through a chemical reaction including a cofactor such as Vitamin B6. Hospodor represents a step forward in the art of decarboxylation of acid forms of cannabinoids.

WIPO publication WO 2012/03478 A1 to Murty et al. describes a cannabinoid formulation operable to avoid hepatic first pass metabolism. It utilizes triglycerides formed from long chain fatty acids to yield improved bioavailability via oral delivery. Such triglycerides are found in coconut oil, according to one embodiment of the invention.

WIPO publication WO 2012/071389 A1 to Rossi et al. describes a shelf-stable cannabinoid composition. It describes how the ration of CBN:THC increases during storage because the CBN is a product of THC degradation. The inventors utilizes the addition of an acid to inhibit THC degradation.

Presently the importance of Cannabidiol (CBD) and its isomers in treating various ailments including cancer, diabetes, seizures, pain, inflammation and other disorders is recognized. CBD is a popular cannabinoid because unlike THC, CBD is non-psychoactive. Accordingly, medical patients and physicians are exhibiting a preference for CBD because patients need to work, drive and function with clarity while undergoing treatment.

Various countries and states in the U.S. are now legalizing hemp as commercial crop. Hemp can be used for fiber production, bio-fuels, food (hemp seed) and also medicine. Hemp plants and extracts thereof, typically contain a high ratio of CBD in the cannabinoid mix. Various strains containing high amounts of CBD are preferred for medicinal purposes. Some hemp plants contain over 10% CBD in the flower of the plant.

Hemp typically contains very little THC, typically between 0.1-0.5% of the whole hemp plant is THC, or THC-A. Various medicinal strains of hemp containing a high CBD content also contain THC in an amount of greater than 0.5%. In some instances, the amount of THC may occur beyond the legal limits imposed on commercial hemp farming. In many regions the legal limit for THC in hemp is between 0.3-0.5%. This legal limit can be met by harvesting the hemp plants prior to maturity, which has the benefit of a reduced THC content, but the drawback of reducing yield.

Medicinal hemp plants can also be grown within the purview of a medicinal marijuana regulatory framework in various jurisdictions. This has the benefit of improving per-plant yield of CBD, but the drawback of additional regulation.

CBD extracted from hemp is beneficial as a nutraceutical, and a heath promoting tonic. CBD has no psychoactivity in typical doses. Its use is remarkably successful in treating children with Dravet syndrome. CBD is a very promising remedy which has no known harmful side-effects, unlike currently used pharmaceutical anti-seizure medication which can have numerous side-effects.

The amount of THC can be reduced in cannabinoid nutraceutical products in any of a variety of ways, without significantly reducing the therapeutic effects of other non-psychoactive cannabinoids. One way to selectively manage or eliminate THC in an extracted product is by processing the extract utilizing a series of fractionating columns. However this is a tedious and expensive process.

What is desired is simple and less expensive process that effectuates selective concentration of cannabinoids. What is also desired is a simple process that yields a lower THC content as a percentage of the cannabinoid mix. What is also desired is a formulation that enables delivery of cannabinoids having a lowered THC content and an increased CBD:THC ratio.

SUMMARY OF THE INVENTION

The present invention includes a novel extraction process that yields a formulated cannabinoid nutraceutical. Preferably the extraction process is applied to hemp, lowers the THC as a percentage of the cannabinoid mix, reduces psychoactivity, and meets regulatory requirements of hemp products. Various methods of the present invention are designed to be performed in a food-grade manufacturing environment and do not require laboratory conditions using vacuum distillation or gas chromatography. This vastly improves production efficiency while reducing equipment costs.

The term extract as used herein should be broadly understood to include both concentrates and extracts of plant substrate material. The term THC and CBD should be construed broadly to include their various isomers.

A method of the present invention includes reducing THC content on percentage basis of the cannabinoid mix in lipid-based extract of *cannabis*. This yields a low-THC product, which has a CBD:THC ratio greater than that of the substrate material. The method includes providing a lipid-based extract of cannabis containing THC, heating the lipid-based extract to 157 to 160° C. to vaporize a first portion of the THC, converting a second portion of the THC to CBN to yield a product containing less than 1 mg of THC per ml.

The step of converting oxidizes the second portion of THC into CBN. This can be accomplished by applying heat at 1 atm of pressure, bubbling an oxidation agent such as pressurized ozone ($O_3$) through the lipid-based extract, or using ultraviolet light to oxidize the second portion of THC into CBN.

When heat is used at 1 atm of pressure, the step of converting a second portion of the THC to CBN is accomplished heating the lipid-based extract to between 130° C.-150° C. for between 5-60 minutes, or preferably between 8-15 minutes, and more preferably 10 minutes.

In one embodiment the cannabis substrate, has less than 1% THC by mass.

The step of providing includes using a multi-stage process including more than one stage of: heating an aqueous solution mixed with *cannabis* substrate material. The aqueous solution has a ratio of a lipid-containing oil to water of between 0.5:10 to 2:10. The lipid oil is heated to at least 121° C. to enable extraction of cannabinoids from the *cannabis* substrate. The aqueous solution is cooled to enable the lipids to form a solid.

In one embodiment the step of providing includes providing a lipid-based extract of *cannabis* containing a first ratio of CBD:THC, the first ratio being at least 1:1 and the step of vaporizing and converting yield a modified lipid-based extract having second ratio of CBD:THC that is greater than the first ratio. The second ratio can be up to a 50:1 ratio, or greater.

The step of vaporizing is preferably accomplished at ambient pressure, i.e. 1 atm of pressure, without the need for a vacuum. This enables cost-effective scaling of the process using standard food processing equipment to create a *cannabis* product.

Preferably, the extract of *cannabis* is an extract of hemp plant having no more than 1.0% THC content by weight of the whole plant.

A multi-stage extraction method assures adequate and selectively optimized cannabinoid concentrations in a *cannabis* product. The multi-stage method for extracting cannabinoids from pre-processed substrate material includes
 a. providing a pre-processed first substrate material containing less than 2% THC by weight;
 b. providing a first lipid solution and combining the first substrate material in the first lipid solution;
 c. heating the first lipid solution at greater than atmospheric pressure to extract cannabinoids from the substrate material into the first lipid solution;
 d. cooling the first lipid solution so cause the first lipids to congeal;
 e. separating the first lipids from the first lipid solution;
 f. providing a second substrate material containing less than 2% THC by mass;
 g. providing a second lipid solution and combing the second substrate material and the first lipids in the second lipid solution;
 h. heating the second lipid solution at greater than atmospheric pressure to extract cannabinoids from the second substrate material into the second lipid solution;
 i. cooling the second lipid solution so cause the second lipids to congeal;
 j. separating the second lipids from the second lipid solution;
 k. post processing to convert THC to CBN and create a *cannabis* product.

The steps g-j repeat at least once to yield a cannabis product. The lipid solution is preferably coconut oil in water, to enable the lipids contained in the coconut oil to bond with the cannabinoids in the substrate material.

It can be appreciated that a product using the present methods can achieve a high CBN:THC ratio, much higher than found in the substrate material used. The CBD:THC ratio is also selectively maximized.

DETAILED DESCRIPTION

Figure 1:
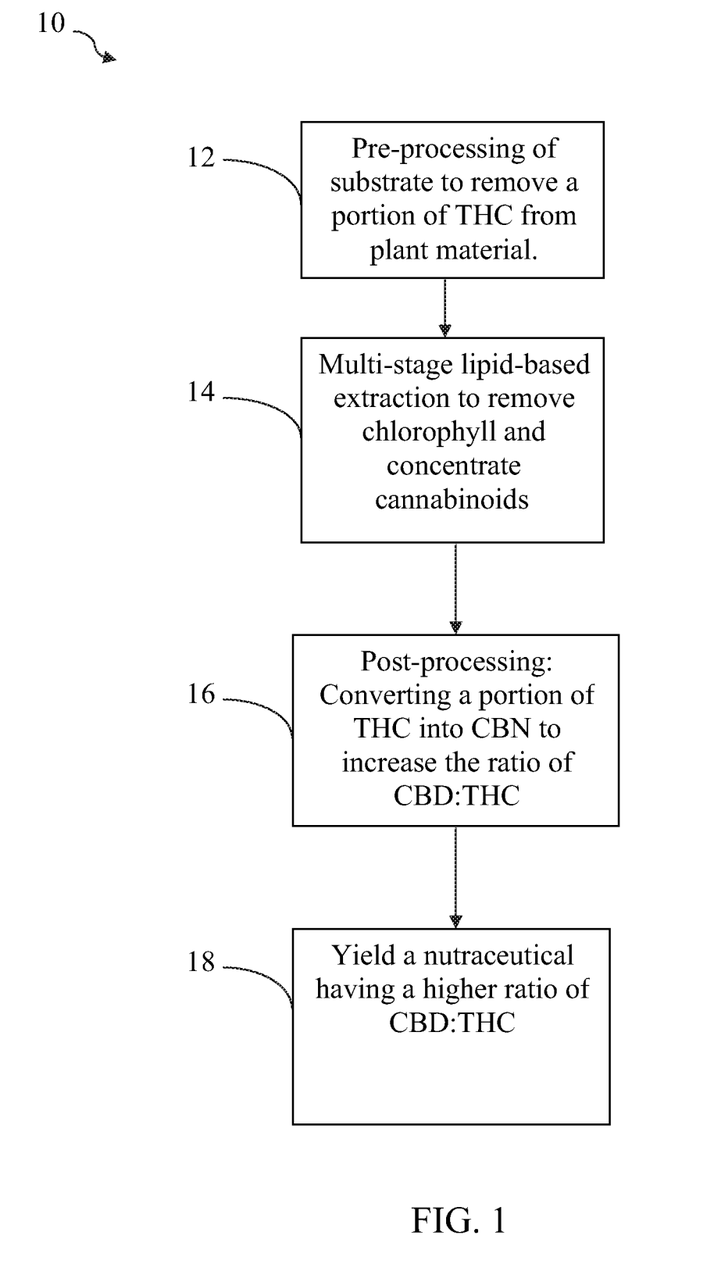
FIG. 1 is a flow chart of a method in accordance with the present invention.

FIG. 1 is a flow chart of a method 10 of manufacturing a nutraceutical in accordance with the present invention. The method 10 includes the step 12 of pre-processing of plant substrate material to remove a portion of trans-Δ9-tetrahydrocannabinol (THC) from the plant substrate material. The plant substrate material may be any cellulosic component of *cannabis*. *Cannabis* includes hemp, marijuana, hybrids and genetically modified variants thereof.

In one embodiment, the plant substrate is marijuana, which is pre-processed in accordance with the step 12 to remove superficial cannabinoid-containing plant elements such as tricombs found on the flower and leaves, and which contain the highest concentrations of THC in the plant.

trans-Δ9-Tetrahydrocannabinol (THC)

The method 10 includes the step 14 of extracting cannabinoids. The step 14 can be repeated a number of times until a desired purity and concentration is achieved. The step 14 preferably includes utilizing a multi-stage lipid-based extraction to remove chlorophyll and waxes, and to concentrate cannabinoids. Although a lipid-based extraction technique is preferred, it can be appreciated that numerous known extraction technique can be used. The step 14 yields a virtually full-spectrum extracted cannabinoid mix in a lipid solution.

The method 10 includes the step 16 of post-processing the extracted cannabinoids. The step 16 performs several func- tions. The first is to volatilize THC and THC-A from the extracted cannabinoids to enable removal of a portion of the THC and THC-A from the extracted cannabinoids. The second function of step 16 is to convert a portion of the THC into CBN. CBD is believed by some to reduce psychoactive effects of THC. In this way the THC content is reduced and the ratio of THC in the cannabinoid mix is decreased. The result is a product that has a higher CBD:THC ratio, reduced psychoactivity and increased attractiveness to consumers in broad markets. Conversion of THC into CBN occurs only significantly when the substrate plant material contains more than 1% THC.

Cannabinol (CBN)

The combination of the step 12 and the step 16 cooperate to reduce psychoactivity of the extracted cannabinoids when used in a nutraceutical or other orally consumable product. The combination of step 12 and step 16 also enables extracted cannabinoids to meet regulatory schemes that require THC content to be within a legally specified limit for nutraceuticals, orally consumed products, suppositories and transdermal products.

The steps 14 and 16 can both achieve decarboxylation of the various acid forms of cannabinoids including Cannabidiol acid (CBD-A), to yield Cannabidiol (CBD), which had improved bioactivity over CBD-A. Together the steps 14 and 16 cooperate to optimize the percentage of cannabinoids that are decarboxylated.

Cannabidiol (CBD)

Figure 2:
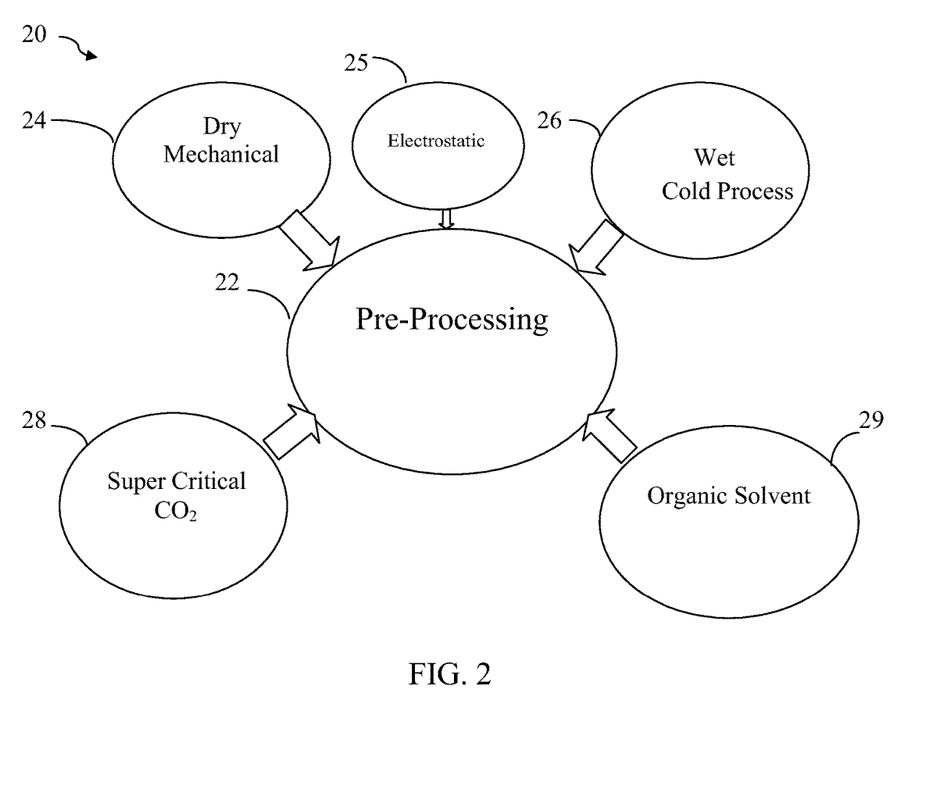
FIG. 2 is a diagram of various pre-processing methods in accordance with the present invention.

FIG. 2 is a diagram 20 of various pre-processing methodologies in accordance with the present invention. The pre-processing step 22 includes, but is not limited to, at least one step selected from the group consisting of: the step 24 dry mechanical processing, the step 25 of electrostatic processing, the step 26 of wet cold processing, the step 28 of supercritical CO2 extraction, the step 29 of organic solvent extraction, or combinations thereof.

The step 24 of dry mechanical processing includes drying *cannabis*, and mechanically shaking the dried *cannabis* with a sieve shaker having a 150-250 μm sieve openings. Alternatively placing the dried *cannabis* in a centrifuge having a similar sieve opening size achieves the dry mechanical processing of step 24 to rapidly remove tricombs from the flower and leaf material of the dried *cannabis*. Because THC is found in the highest concentrations in the tricombs, this step 24 of dry mechanical processing quickly and efficiently removes a portion of THC from dried *cannabis* material. The dried *cannabis* used herein includes various parts of the *cannabis* plant including leaves and flowers.

The step 25 of electrostatic processing includes passing dry *cannabis* material on a conveyer and feeding it through a thin gap between two parallel planar electrodes of an electrostatic separator. The tricombs are thus separated from the dry *cannabis* material.

The step 26 of a wet cold process includes adding dry cannabis to an aqueous solution and cooling, actuation such as shaking or spinning releases tricombs through screens of various sizes to remove the tricombs. The residual *cannabis* plant material is dried for further processing in accordance with the present invention.

The step 28 of super critical CO2 extraction includes applying high pressure CO2 to the dried *cannabis* material to extract a portion of the cannabinoids. While this method is commonly used in the medical marijuana industry and it extracts most cannabinoids from the plant material, it is not 100% efficient. Accordingly, some cannabinoids remain in the substrate material post-extraction. These residual cannabinoids can be recovered by further processing in accordance with the present invention.

Importantly, the present invention can utilize post extraction material that is typically considered waste to achieve a concentrated lipid-based *cannabis* product.

The step 29 of using an organic solvent can include ethyl alcohol extraction of cannabinoids. A rapid extraction using ethyl alcohol will remove tricombs and superficial cannabinoids from plant material, and enable further process steps in accordance with the present invention to further extract and process the residual cannabinoids in the plant material. Again, the present invention can utilize post extraction *cannabis* that is typically considered waste to achieve a lipid-based *cannabis* product.

Various additional solvents used for extraction of cannabinoid also includes propane, butane, and other solvents.

Figure 3:
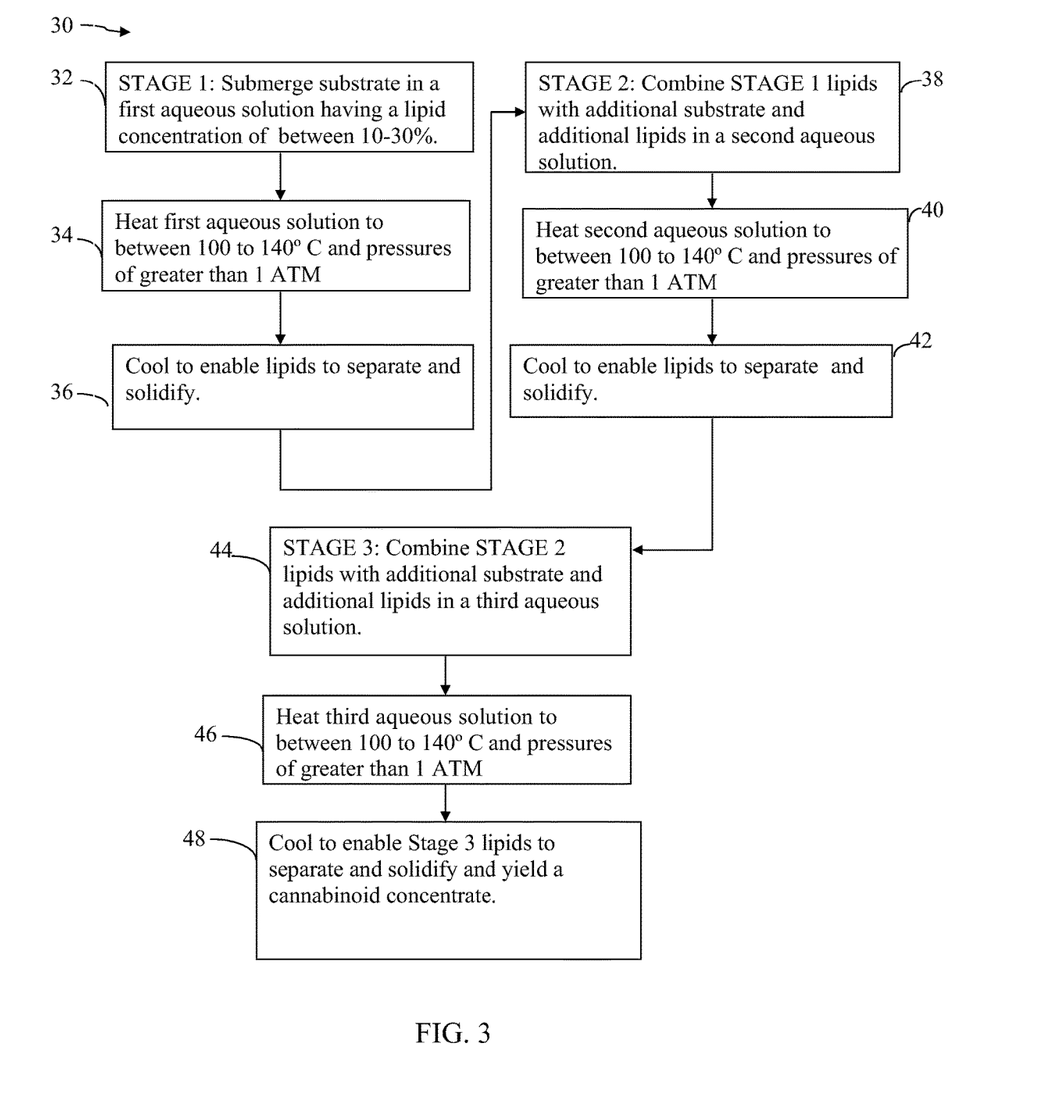
FIG. 3 is a flow chart of an extraction method in accordance with the present invention.

FIG. 3 is a flow chart of an extraction method 30 in accordance with the present invention. The method 30 is a lipid based extraction method that yields a *cannabis* product. An advantage of using a lipid based extraction is that it efficiently extracts cannabinoids residual from *cannabis* plant material that is: post extraction waste, pre-processed in another manner, or unprocessed or dried *cannabis* substrate material. The method 30 can be used to extract cannabinoids from plants other than *cannabis*, including hops.

Another advantage is that the lipid based approach preferably uses organic food grade lipids that are non-toxic. A further advantage of lipid-based extraction is that there is reduced fire or explosion hazard as compared to butane, propane, alcohol and other solvent based extraction techniques. Another advantage of lipid-based extraction over $CO_2$ extraction techniques is that the dangerously high pressures (thousands of psi) associated with $CO_2$ extraction techniques is not required.

The method 30 is a multi stage method. The method 30 preferably includes three stages that commence with step 32, step 38 and step 44, respectively. These extraction stages enable cannabinoids to bond to lipids and inhibit volatilization of cannabinoids by applying pressure at each stage. Multiple stages assures adequate concentrations of cannabinoids in a resulting lipid-based *cannabis* product.

The step 32 begins STAGE 1 and includes submerging substrate in a first aqueous solution having a lipid concentration of between 5-40%. Preferably, the first aqueous solution includes between 5-20% of a lipid-containing oil, such as coconut oil, and 80-95% purified water.

The substrate is preferably dried cannabinoid-containing cellulosic plant material such as leaves or flowers. Cannabinoid-containing plants include *cannabis* and its subspecies and varieties including Hemp, Marijuana, variants, hybrids, and genetic modifications thereof. Cannabinoids are defined substances that effect the CB1 or CB2 receptors in humans. It can be appreciated that cannabinoids can be contained in numerous other plants, including hops. The present invention can be applied to non-cannabis plants that contain cannabinoids.

The step 34 heats the first aqueous solution to between 100-140° C. and at pressures of greater than 14.7 psi. Preferably the pressure is between 5-25 psi above atmospheric pressure. Heating the first aqueous solution enables the lipids to bond with the cannabinoids. Pressure makes this process more efficient and inhibits volatilization of various cannabinoids.

The step 36 cools the first aqueous solution to ambient temperature i.e. approximately 22° C. At this temperature the coconut oil solidifies to isolate the STAGE 1 lipids from the water in the first aqueous solution, which are removed to enable STAGE 2.

The step 38 begins STAGE 2, where the STAGE 1 lipids are combined with a second aqueous solution. The second aqueous solutions includes a lipid oil having a concentration of between 5-40%. Preferably, the second aqueous solution is between 5-20% of a lipid oil, such as coconut oil, and 80-95% purified water. Additional substrate material is added.

The step 40 heats the second aqueous solution to between 100-140° C. and at pressures of greater than 14.7 psi. Preferably the pressure is between 5-25 psi above atmospheric pressure. Heating the third aqueous solution enables the lipids to bond with the cannabinoids. Pressure makes this process more efficient and inhibits volatilization and escape of various terpines, diterpenes and other *cannabis* components.

The step 42 cools the second aqueous solution to ambient temperature i.e. approximately 22° C. At this temperature the coconut oil congeals to isolate the STAGE 2 lipids from the water in the second aqueous solution, which are removed to enable STAGE 3.

Step 44 begins STAGE 3 by combining the STAGE 2 lipids with additional lipids and additional substrate in a third aqueous solution including a lipid concentration of between 5-40%. Preferably, the third aqueous solution is between 5-20% of a lipid-containing oil, such as coconut oil, and 80-95% purified water.

The step 46 heats the third aqueous solution to between 100-140° C. and at pressures of greater than 14.7 psi. Preferably the pressure is between 5-25 psi above atmospheric pressure. Heating the third aqueous solution enables the lipids to bond with the cannabinoids.

The step 42 cools the third aqueous solution to ambient temperature i.e. approximately 22° C. At this temperature the coconut oil congeals to isolate the STAGE 3 lipids from the water in the third aqueous solution.

This three stage process provides sufficient purification of cannabinoids to yield a concentrated cannabinoid mix in a lipid solution, where the cannabinoid mix generally matches the cannabinoid mix in the substrate materials used for the method 30 except that a good portion of the acid forms of cannabinoids convert to non-acid forms by decarboxylation.

After each stage mechanical pressure rids much of the aqueous solution from the substrate material. In one embodiment, a vacuum pump is applied to draw residual aqueous solution from the mix of substrate material and aqueous solution prior to cooling the aqueous solution. This assures the maximum amount of cannabinoids are removed from the substrate material.

There are various reasons that the method 30 utilizes coconut oil as the lipid source. Coconut oil is useful because the temperature ranges required for volatilization of THC and conversion of THC to CBN are quite specific and the lipid source needs to be selected to accommodate such temperatures. In particular, temperatures of approximately 132° C. are required to reduce THC to CBN at certain pressures. Coconut oil can endure temperatures of between 177° C. and 204° C. before reaching the smoke point depending on the level of refinement of the coconut oil. Additionally, coconut oil is solid at room temperature i.e. 25° C., which is ideal for separating the cannabinoid infused lipids from an aqueous solution at ambient temperatures. Coconut oil is also a well-known and widely accepted functional food, therapeutic in its own right for various ailments. Consumers that choose nutraceuticals for health purposes tend to also prefer natural and healthy constituents as a nutraceutical carriers.

It can be appreciated that various other lipid sources can be used, and that particular lipid sources can be modified or processed to perform within the preferred temperature range requirements of the present invention. For example, Coco-butter oil, canola oil, safflower oil, olive oil, sunflower oil, corn oil, soybean oil, butter, ghee and lard could be substituted for the coconut oil.

The multi-stage extraction process efficiently extracts virtually all cannabinoids from plant substrate material, this process is so efficient that it enables waste plant material that has already been processed into extracts to be used. Accordingly the present invention enables a zero-waste process as an add-on to a facility that performs extractions of cannabinoid substrate materials.

In one embodiment of the invention, where the temperature ranges are reduced through application of a vacuum to volatilize THC and THC-A, the lipid source can be a lipid source having a lower smoke point than coconut oil.

The following is an example of the extraction method 30:

Example 1

Mix 1600 grains of dried *cannabis* substrate (leaves and flowers), ½ gallon of coconut oil, and 4 gallons of water. This yields an approximate ratio of 1:8 lipid oil to water. This ratio produces a concentration of no less than 25 mg of nearly full spectrum extracted cannabinoids per 1 ML of coconut oil. The final extracted oil can then be encapsulated, and taken internally, or applied topically. A capsule could be made of gelatin, plant cellulose, or combined with starch into a pressed pill.

Stage 1:
A. Mix 1600 grams of dried *cannabis*, ½ gallon of coconut oil, and 4 gallons of water is added to the pressure cooker. Heat under pressure at 15 psi at 121° C. degrees for 6 hours.
B. Reduce heat and pressure to 7 psi above atmospheric at 107° C. for an additional 14 hours.
C. The vessel is brought down to atmospheric pressure at 93° C.
D. Saturated substrate is then squeezed of all liquid using mechanical pressure.

E. All liquid is saved and put in a separate stainless steel pot.
F. The stainless pot with liquid is chilled to within 1-10° C. 18 hours to separate water from oil.
G. Remove the solid layer of congealed coconut oil, and place the oil in a separate clean pressure cooker.

Stage 2:
A. Along with the congealed oil that was placed in the clean pressure cooker above, add 1600 grains of dried *cannabis*, and 4 gallons of water. Seal vessel and bring to a 15 psi above atmospheric pressure at 121° C. for 6 hours.
B. The heat source is then set to 7 psi at 107° C. for an additional 14 hours.
C. The vessel is brought down to 0 psi at 93° C.
D. Once at 93° C., saturated substrate material is then squeezed of all liquid using mechanical pressure.
E. All liquid is saved and put in a separate stainless steel pot and chilled to within 1-10° C. 18 hours.
F. After 18 hours, the coconut oil has congealed, separating from the water. At that point, remove the solid layer of congealed coconut oil, and place the oil in a separate clean pressure cooker.

Stage 3:
A. Along with the congealed oil of STAGE 2, add 1600 grams of dried *cannabis,* 4 gallons of water, PLUS an additional 1 liter of fresh coconut oil. Seal vessel and bring to a 15 psi above atmospheric pressure at 121° C. for 6 hours. The additional coconut oil in this stage is added to insure the saturation availability of the entire mixture.
B. The heat source is then set to 7 psi above atmospheric pressure at 107° C. for an additional 14 hours.
C. The vessel is brought down to 0 psi at 93° C. and saturated substrate material is then squeezed of all liquid using mechanical pressure, or with a vacuum.
D. All liquid is saved and put in a separate stainless steel pot and chilled to within 1-10° C. 18 hours.
E. Remove the solid layer of congealed coconut oil to yield concentrated *cannabis* product in a lipid solution.

Figure 4:
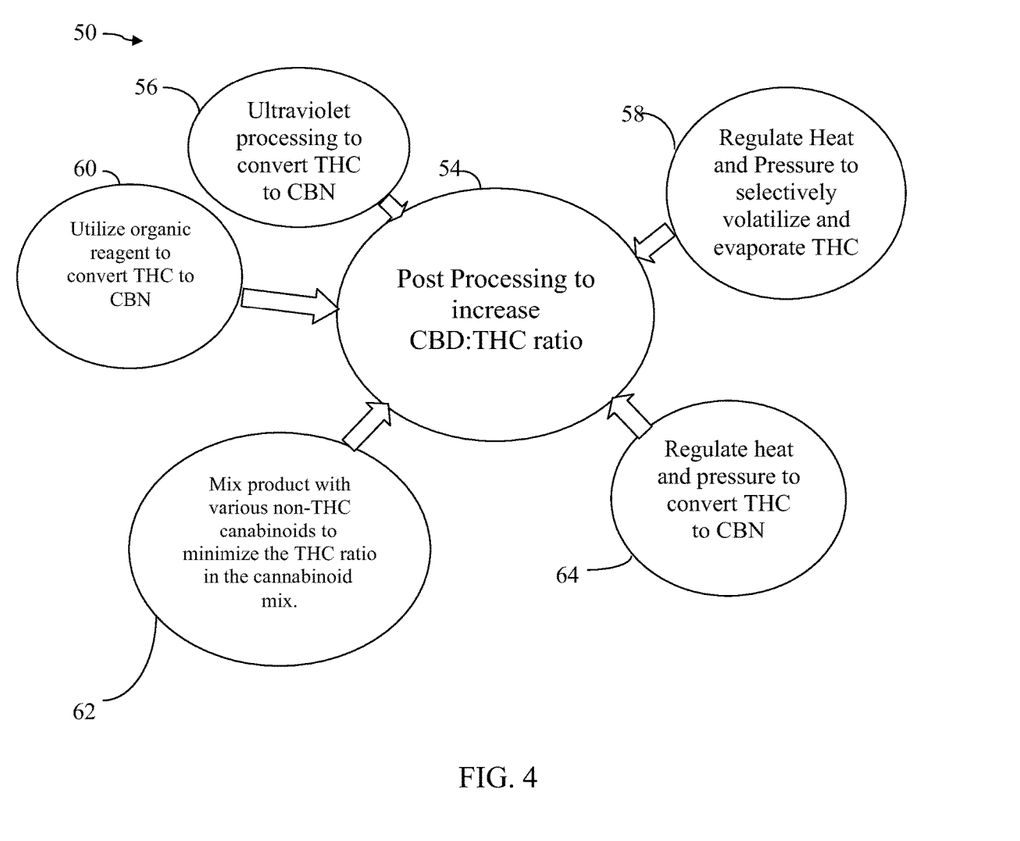
FIG. 4 is a diagram of various post-processing methods in accordance with the present invention.

FIG. 4 is a diagram of a post-processing method 50 in accordance with the present invention. The method 50 includes step 54 to increase the CBD:THC ratio of extracted cannabinoids. An example of extracted cannabinoids includes the extracted *cannabis* product in a lipid solution as described above.

The method 50 increases the CBN:THC ratio of extracted cannabinoids utilizing at least one method selected from the group consisting of: the step 56 of directing ultraviolet light through the extracted cannabinoids to convert THC-A and THC to CBN; the step 58 of regulating heat and pressure to selectively volatilize THC-A and THC; the step 60 of utilizing an organic reagent to convert THC to THC-A to CBN; the step 62 of mixing the extracted cannabinoids with various non-THC cannabinoids including CBN to minimize, or reduce, the THC ratio in the cannabinoid mix; and the step 64 of regulating heat and pressure to convert THC to CBN.

The step 58 also regulates humidity, which can influence the vaporization temperature of THC. Preferably the step 58 and 64 are combined and applied to the extracted *cannabis* product to volatilize a first portion of the THC and convert a second portion of THC into CBN. Volatilization (Vaporization) Temperatures at 1 atm (14.7 psia) of pressure for various cannabinoids is expressed in Table 1:

TABLE 1

| Cannabinoid | Vaporization Temperature ° C. at 14.7 psia (1 atm) |
| --- | --- |
| Delta-9-THC | 157 |
| Delta-8-THC | 175-178 |
| CBD | 160-180 |
| CBN | 185 |
| CBC | 220 |
| THCV | 220 |

The vaporization temperature of THC varies considerably with pressure. Table 2 reveals that the present invention can include utilizing a vacuum effectuate volatilization of THC. The term boiling point is used in Table 2 and refers to the volatilization or vaporization point as used herein.

As shown in Table 2, at a temperature of 40° C. and at a pressure of 0.0145 psia, THC will volatilize or boil. Accordingly, in a variation of the present invention, the pressure may be adjusted to remove THC from the extracted cannabinoids at temperatures and pressures expressed in Table 2.

TABLE 2

| % Vacuum | Torr (mm Mercury) | Micron | Psia, (lb/in²) abs | Inches Mercury Absolute | Inches Mercury Gauge | kPa abs | Boiling Point delta 9 THC |
| --- | --- | --- | --- | --- | --- | --- | --- |
| 0.0 | 760.0 | 760,000 | 14.7 | 29.92 | 0.00 | 101.4 | 157 C./315 F. |
| 1.3 | 750.0 | 760,000 | 14.5 | 29.5 | 0.42 | 99.9 | 157 C./315 F. |
| 1.9 | 735.6 | 735,600 | 14.2 | 28.9 | 1.02 | 97.7 | 156 C./312.6 F. |
| 7.9 | 700.0 | 700,000 | 13.5 | 27.6 | 2.32 | 83.5 | 155 C./311 F. |
| 21.0 | 600.0 | 600,000 | 11.6 | 23.6 | 6.32 | 79.9 | 152 C./305.6 F. |
| 34.0 | 500.0 | 500,000 | 6.7 | 19.7 | 10.22 | 68.7 | 148 C./296.4 F. |
| 47.0 | 400.0 | 400,000 | 7.7 | 16.7 | 14.22 | 53.2 | 143 C./289.4 F. |
| 50.0 | 380.0 | 380,000 | 7.3 | 16.0 | 14.92 | 50.8 | 142 C./287.6 F. |
| 61.0 | 300.0 | 300,000 | 5.8 | 11.8 | 18.12 | 40 | 137 C./278.6 F. |
| 74.0 | 200.0 | 200,000 | 3.9 | 7.85 | 22.07 | 29.6 | 128 C./262.4 F. |
| 87.0 | 100.0 | 100,000 | 1.83 | 3.94 | 25.98 | 13.3 | 115 C./239 F. |
| 88.0 | 90.0 | 90,000 | 1.74 | 3.54 | 26.38 | 12 | 113 C./235.4 F. |
| 89.6 | 80.0 | 80,000 | 1.85 | 3.15 | 28.77 | 10.7 | 111 C./231.8 F. |
| 90.8 | 70.0 | 70,000 | 1.35 | 2.76 | 27.16 | 9.3 | 108 C./226.4 F. |
| 92.1 | 60.0 | 60,000 | 1.15 | 2.36 | 27.55 | 6 | 105 C./231 F. |
| 93.0 | 61.7 | 61,700 | 1.00 | 2.03 | 27.89 | 6.9 | 103 C./217.4 F. |
| 93.5 | 50.0 | 50,000 | 0.97 | 1.97 | 27.95 | 6.7 | 103 C./215.6 F. |
| 94.8 | 40.0 | 40,000 | 0.77 | 1.57 | 28.35 | 5.3 | 98 C./208.4 F. |
| 96.1 | 30.0 | 30,000 | 0.58 | 1.18 | 28.74 | 4 | 93 C./199.4 F. |

TABLE 2-continued

| % Vacuum | Torr (mm Mercury) | Micron | Psia, (lb/in²) abs | Inches Mercury Absolute | Inches Mercury Gauge | kPa abs | Boiling Point delta 9 THC |
|---|---|---|---|---|---|---|---|
| 96.6 | 25.4 | 25,400 | 0.49 | 1.00 | 28.92 | 3.4 | 91 C./195.8 F. |
| 97.4 | 20.0 | 20,000 | 0.39 | 0.785 | 29.14 | 2.7 | 87 C./188.6 F. |
| 98.7 | 10.0 | 10,000 | 0.193 | 0.394 | 29.53 | 1.3 | 76 C./168.8 F. |
| 99.0 | 7.6 | 7,600 | 0.147 | 0.299 | 29.62 | 1.0 | 72 C./161.6 F. |
| 99.9 | 1.0 | 1,000 | 0.01934 | 0.03837 | 29.68 | 0.13 | 44 C./131.2 F. |
| 99.9 | 0.75 | 750 | 0.0145 | 0.0295 | 29.69 | 0.1 | 40 C./104 F. |
| 99.99 | 0.10 | 100 | 0.00193 | 0.00394 | 29.916 | 0.013 | 17 C./62.6 F. |
| 99.999 | 0.01 | 10 | 0.000193 | 0.000394 | 29.9196 | 0.0013 | −5 C./23 F. |
| 100 | 0.00 | 0 | 0 | 0 | 29.92 | 0 | |

Figure 5:
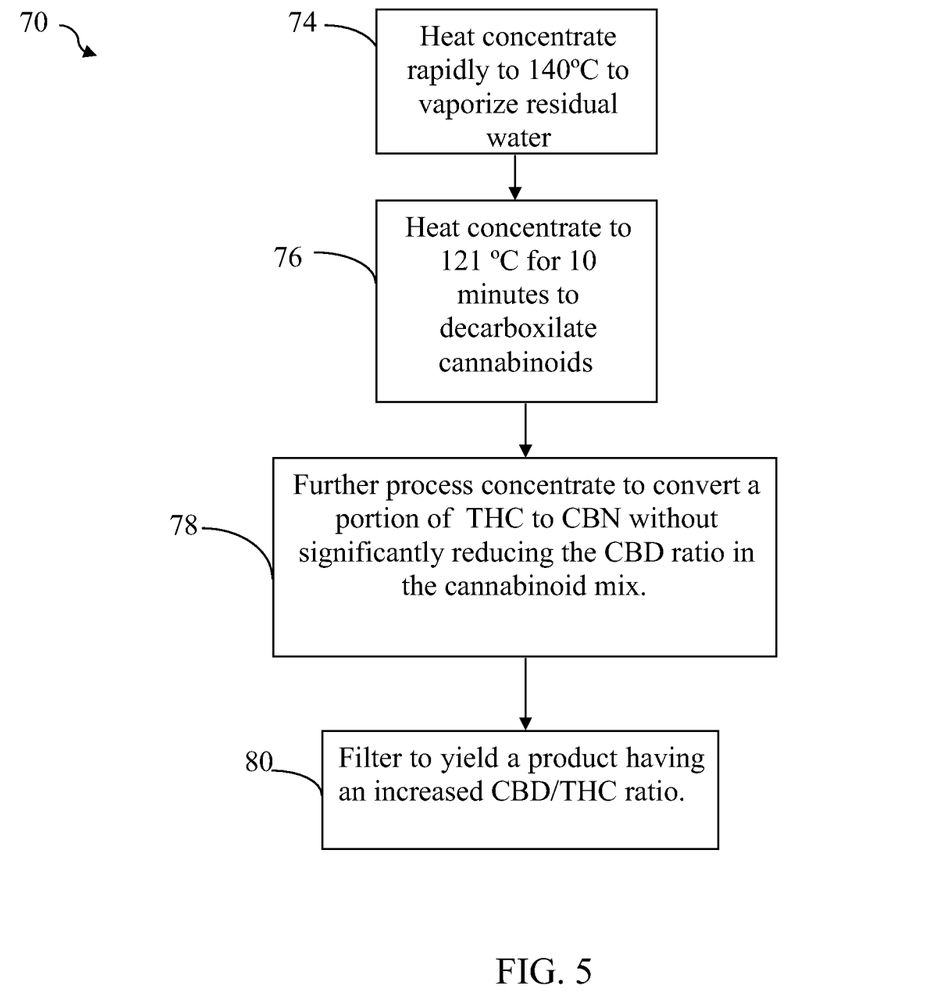
FIG. 5 is a method of post-processing in accordance with the present invention.

FIG. 5 is a preferred method 70 of post-processing in accordance with the present invention. The method 70 includes the step 74 of heating the extracted cannabis product rapidly to at least 140° C. to boil off any residual water in the lipid oil. Further increasing the temperature to the vaporization temperature of THC i.e. 157° C. begins to volatilize the THC. The further increasing of the temperature should not exceed the vaporization temperature of CBD, which is between 160-180° C. The regulation of temperature enables both water and THC to volatilize and evaporate from the lipid oil. The CBD and CBN concentration increase as a percentage in the cannabinoid mix due to the volatilization and evaporation of the THC.

It can be appreciated that temperatures within the range of vaporization of CBD could be utilized in accordance with the present invention, with the advantage of improving the vaporization volume of THC and its isomers, but with the disadvantage of reducing the CBD volume. In a preferred embodiment, a high CBD product is sought so that reducing the CBD content is not preferred. However, in an alternate embodiment where concentrations of various other cannabinoids including CBN, CBC and THCV are sought, then it would be advantageous to increase the temperature to beyond the CBD vaporization temperature.

It can also be appreciated that application of pressure changes the vaporization temperature of various cannabinoids. While it is preferred to utilize the present invention at 1 atm of pressure, it can be appreciated that the present invention can be implemented by changing the pressures and corresponding temperatures, respectively.

The step 76 of heating the concentrate to 121° C. for at least 10 minutes to decarboxilate any remaining non-decarboxilated cannabinoids, the step 78 of further processing the concentrate to convert a portion of THC to CBN without significantly reducing the CBD ratio in the cannabinoid mix, and the step 80 of filtering to yield a product having an increased CBN/THC ratio.

Although some CBD and other cannabinoids may be volatilized or transformed during this process, there will be residual CBD in the cannabinoid mix to achieve a high-CBD and low-THC product, or a THC-free product having no detectable levels of THC.

Test Results

All cannabinoids in their acid forms (those ending in "-A") can be converted to their non-acid forms through a process called decarboxylation when the sample is heated. The molecules lose mass through this process, and thus to find the total theoretical active cannabinoids you must multiply the acid forms by 87.7%. For example, THC-A can be converted to active THC using the formula: THC-A× 0.877=THC. The Max THC for the sample is: Max THC= (THC-A×0.877)+THC. This method has been validated according to the principles of the International Conference on Harmonization.

Similarly, CBD-A can be converted to active CBD and the yield is determined using the yield formula: CBD-A× 0.877=CBD. Also the maximum amount of CBD yielded, i.e max CBD for the sample is: Max CBD=(CBD-A×0.877)+ CBD.

Table 3 below shows the analysis of the cannabinoid mix in a particular Hemp strain sample utilized as a *cannabis* substrate in accordance with the present invention. The sample included only flower material. Often when THC content in hemp strains is determined by government tests, the whole plant is utilized in the test. Here only the flower portion, containing the highest concentration of cannabinoids, is tested. This particular strain analyzed in Table 3 is a proprietary strain owned by CBDRX Incorporated of Pueblo, Colo. The strain is known as CBDRX cultivar 18. The ratio of max CBD:THC is approximately 22:1 by percentage of the cannabinoid mix.

TABLE 3

| Test | Weight % |
|---|---|
| CBD-V | <0.001% |
| CBD-A | 21.46% |
| CBG | <0.001% |
| CBD | 0.39% |
| THC-V | <0.001% |
| CBN | <0.001% |
| THC | 0.03% |
| CBC | 0.03% |
| THC-A | 0.96% |
| Max THC | 0.88% |
| Max CBD | 19.21% |
| Total Active | 0.46% |
| Total | 22.88% |

Noteworthy is that there is a max THC of 0.88% and a nearly undetectable amount of CBN percentage on a mass basis of the cannabinoid mix in this substrate sample. The max CBD value is 19.21% which is quite high relative to other medicinal strains of hemp.

Table 4 shows test results for a concentrated cannabinoid product created from the substrate material of Table 3 in accordance with the present invention. Note that the Max THC is 0.14% and the max CBD is 3.81%. Note max CBD equals the CBD value. The max THC equals the THC value. These numbers indicate that full decarboxylation of CBD-A and THC-A has been accomplished. This yields a ratio of max CBD:THC of approximately 27:1 by percentage of the cannabinoid mix.

It can be appreciated that the CBD:THC ratio influences therapeutic efficacy of the product and can be adapted to virtually eliminate psychoactivity of the product. Also, current regulatory framework favors products having a cannabinoid mix having with less than 0.3-0.5% THC, which typically yields a non-psychoactive product. Utilizing a method that does not require laboratory conditions using vacuum distillation or gas chromatography to improve the CBD:THC ratio vastly improves production efficiency while reducing costs.

THC and THC-A are precursors to formation of CBN. The CBN percentage is not detectable because there are undetectably low levels of THC and THC-A presented in the substrate sample reflected in Table 3, and because of the undetectably low levels of CBN originating in the same sample. In alternate embodiments of the present invention, where there are higher levels of THC and THC-A presented in the substrate sample, the CBN percentage would be increased and the CBN:THC ratio in the cannabinoid product would be increased from the ratio detected in the substrate sample.

TABLE 4

| Test | Weight % |
| --- | --- |
| CBD-V | <0.001% |
| CBD-A | <0.001% |
| CBG | 0.13% |
| CBD | 3.81% |
| THC-V | <0.001% |
| CBN | <0.001% |
| THC | 0.14% |
| CBC | 0.20% |
| THC-A | <0.001% |
| Max THC | 0.14% |
| Max CBD | 3.81% |
| Total Active | 4.28% |
| Total | 4.28% |

Comparing the max CBD:THC ratios shows that the present invention yields an increase in the max CBD:THC ratio from flower substrate sample to the concentrated product. This can accomplished without the need for a vacuum distillation, fractionating columns or a gas chromatography system. The change in the max CBD:THC ratio from the substrate material to the *cannabis* product is a change from approximately 22:1 to 27:1.

When utilizing higher THC content substrate, pre-processing in conjunction with the extraction and post processing yields more dramatic results, and higher concentrations of CBN by weight in the cannabinoid mix. Accordingly, in one aspect of the present invention, a concentrated product having an improved (increased) CBN:THC ratio is achieved by beginning with a substrate having a greater amount of max THC, e.g. between 2%-25% max THC.

A product created in accordance with the present invention yields an improved product having higher CBD:THC ratio and a higher CBN:THC ratio than the substrate material input to the process. Because the material input is non-decarboxilated, the max THC values are determinative of this ratio upon input. Also the max CBD values are similarly determined. The CBN values are selectively determined by varying the substrate, the process time and temperature of the post-process parameters.

The following are examples of the post processing method 50:

Example 2

Post Processing to Decarboxilate and Reduce THC
A. After STAGE 3 is complete and the coconut oil congeals and separates from the water, place congealed coconut oil in a clean stainless steel pot. Heat oil rapidly to above 141° C., preferably above the vaporization temperature of THC i.e. 157° C. and below the vaporization temperature of CBD, which is between 160-180° C. This process will remove any remaining water content in the oil and volatilize a portion of THC contained in the concentrated *cannabis* product.
B. Continue heating the oil at 121° C. for an additional 10 min to activate cannabinoids, causing most of any remaining non-decarboxilated portion of the cannabinoids to decarboxilate.
C. Allow the oil to cool to 82° C. and pour through a filter no greater than 20 microns.
D. The oil should be nearly 100% water free and most cannabinoids will be decarboxilated. Concentration of cannabinoids in the cannabinoid product is preferably no less than 25 mg of cannabinoid per 1 ML of coconut oil.
E. The oil can then be encapsulated and administered internally or applied topically. A capsule could be made of gelatin, plant cellulose, or combined with starch into a pressed pill.

Example 3

Post Processing to Increase CBD:THC Ratio
A. After STAGE 3 is complete and all oil separated, place congealed coconut oil in a clean stainless steel pot. Heat oil rapidly to above 141° C., preferably above the vaporization temperature of THC i.e. 157° C. and below the vaporization temperature of CBD, which is between 160-180° C. This process will remove the remaining water content in the oil and some THC content will be volatilized. Although some CBD may be volatilized, preferably the *cannabis* substrate used in the various extraction stages is from a hemp strain containing at least a 8:1 ratio of CBD:THC so even with some degradation of CBD, there is a significant residual amount of CBD in the cannabinoid mix.
B. Continue heating the oil at 132° C. for an additional 10 min to convert a portion of THC to CBN.
C. Allow the oil to cool to 82° C. and pour through a filter no greater than 20 microns.
D. The oil should be 100% water free and most cannabinoids will be decarboxilated. The cannabinoid concentration is preferably is not less than 25 mg of cannabinoids per 1 ML of coconut oil.
E. The oil can then be encapsulated and administered internally or applied topically. A capsule could be made of gelatin, plant cellulose, or combined with starch into a pressed pill.

Example 4

Post Processing to Increase CBD:THC Ratio
A. After STAGE 3 is complete and all oil separated, place congealed coconut oil in a clean stainless steel pot. Heat oil rapidly to at least 141° C. This process will remove the remaining water content in the oil.
B. Continue heating the oil at 132° C. for 10-60 minutes to convert a portion of THC to CBN and to volatilize another portion of THC.

C. Allow the oil to cool to 82° C. and pour through a filter no greater than 20 microns.
D. The oil should be 100% water free and most cannabinoids will be decarboxilated. Concentration should be no less than 25 mg of cannabinoid per 1 ML of coconut oil.
E. The final extracted oil can then be encapsulated and administered internally or applied topically. A capsule could be made of gelatin, plant cellulose, or combined with starch into a pressed pill.

Example 5

Post Processing to Increase CBD:THC Ratio
A. After STAGE 3 is complete and all oil separated, place congealed coconut oil in a clean stainless steel pot. Heat oil rapidly to at least 141° C. This process will remove the remaining water content in the oil.
B. Continue heating the oil at 132° C. for an 10-60 minutes to convert a portion of THC to CBN and to volatilize another portion of THC.
C. Allow the oil to cool to 82° C. and pour through a filter no greater than 20 microns.
D. The oil should be 100% water free and most cannabinoids will be decarboxilated. Concentration should be no less than 25 mg of cannabinoid per 1 ML of coconut oil.
E. The final extracted oil can then be subjected to a vacuum and heated to 40° C. at a pressure of 0.0145 psia to remove any residual THC. The extracted oil is then encapsulated and can be administered internally or applied topically. A capsule could be made of gelatin, plant cellulose, or combined with starch into a pressed pill.

I claim:

1. A method for increasing the ratio of cannabinol to trans-Δ9-tetrahydrocannabinol in a coconut oil-based extract of *cannabis* consisting essentially of:
    providing a coconut oil-based extract of *cannabis* containing trans-Δ9-tetrahydrocannabinol and having a first cannabinol to trans-Δ9-tetrahydrocannabinol ratio;
    heating the coconut oil extract to 157° C. to 160° C. to vaporize a first portion of the trans-Δ9-tetrahydrocannabinol;
    converting a second portion of the trans-Δ9-tetrahydrocannabinol to cannabinol by heating the coconut oil extract to 130° C.-150° C. for between 5-60 minutes under vacuum conditions to yield a coconut oil-based extract product having a second cannabinol to trans-Δ9-tetrahydrocannabinol ratio, and
    wherein, the second cannabinol to trans-Δ9-tetrahydrocannabinol ratio is greater than the first cannabinol to trans-Δ9-tetrahydrocannabinol ratio.

2. The method of claim 1, wherein the step of converting is accomplished at approximately 1 atm of pressure.

3. The method of claim 1, wherein the step of converting is accomplished by heating the coconut oil extract for between 8-15 minutes.

4. The method of claim 1, wherein the step of providing is performing a multi stage extraction of *cannabis*.

5. The method of claim 1, wherein the trans-Δ9 -tetrahydrocannabinol is both trans-Δ9-tetrahydrocannabinol acid and non-acid forms of trans-Δ9-tetrahydrocannabinol.

6. A method for increasing the ratio of cannabinol to trans-Δ9-tetrahydrocannabinol in a coconut oil extract of *cannabis*, consisting essentially of:
    providing *cannabis* having a first ratio of cannabinol to trans-Δ9-tetrahydrocannabinol and coconut oil;
    utilizing a multi stage coconut oil extraction process with the coconut oil to extract cannabinoids from the *cannabis* to yield a coconut oil extract of *cannabis;*
    heating the coconut oil extract to between 157° C. to 160° C. to vaporize a first portion of the trans-Δ9-tetrahydrocannabinol; and
    heating the coconut oil extract to 130° C.-150° C. for between 5-60 minutes to convert a second portion of the trans-Δ9-tetrahydrocannabinol to cannabinol under vacuum conditions;
    whereby converting creates a *cannabis* product having second ratio of cannabinol to trans-Δ9-tetrahydrocannabinol that is greater than the first ratio of cannabinol to trans-Δ9-tetrahydrocannabinol.

7. The method as set forth in claim 6, wherein the *cannabis* has no detectable amount of trans-Δ9-tetrahydrocannabinol.

8. The method as set forth in claim 7, wherein the *cannabis* has greater than 0.001% cannabinol.

9. The method as set forth in claim 6, wherein multi stage coconut oil extraction process heats and cools the lipid-solution more than once.

* * * * *